United States Patent [19]
Smith et al.

[11] Patent Number: 5,797,961
[45] Date of Patent: Aug. 25, 1998

[54] RADIUSED HOLLOW CUTTING EDGE NEEDLE

[75] Inventors: Daniel J. Smith, Manalapan; Carl Gucker, Branchburg; Zivko Elik, Bound Brook; Paul Parisi, Bridgewater; Randolph Ruetsch, Branchburg; William McJames, Belle Mead; Emil Richard Skula, Wayne, all of N.J.

[73] Assignee: Ethicon, Inc., Somerville, N.J.

[21] Appl. No.: 916,964

[22] Filed: Aug. 19, 1997

Related U.S. Application Data

[63] Continuation of Ser. No. 601,899, Feb. 15, 1996, abandoned.
[51] Int. Cl.⁶ .................................................. A61B 17/06
[52] U.S. Cl. ........................... 606/222; 606/223; 289/16; 112/222
[58] Field of Search ................................ 606/222, 223, 606/225, 226; 66/116, 117; 223/102, 103, 104; 163/5; 289/16; 112/222

[56] References Cited

U.S. PATENT DOCUMENTS 1,599,059  9/1926  Morton .
3,038,475  6/1962  Orcutt .
4,660,559  4/1987  McGregor et al. .......... 128/339
5,342,397  8/1994  Guido ......................... 606/222

FOREIGN PATENT DOCUMENTS

3712163 A1  10/1987  Germany .
3841443C1   4/1990   Germany .
1428360     7/1988   U.S.S.R. .
582276      2/1994   United Kingdom .

Primary Examiner—Michael Powell Buiz
Assistant Examiner—Tina T. D. Pham
Attorney, Agent, or Firm—Emil Richard Skula

[57] ABSTRACT

A cutting edge surgical suture needle. The suture needle is an elongated member having a proximal suture mounting end and a distal piercing tip. The distal section of the needle has a cross-section having a top side with opposed edges. The cross-section also has opposed curved concave lateral sides having top edges and bottom edges. The top edges of the concave sides and the opposed sides of the top side are coextensive and form cutting edges. The bottom edges of the opposed concave sides are coextensive and form a bottom cutting edge.

15 Claims, 9 Drawing Sheets

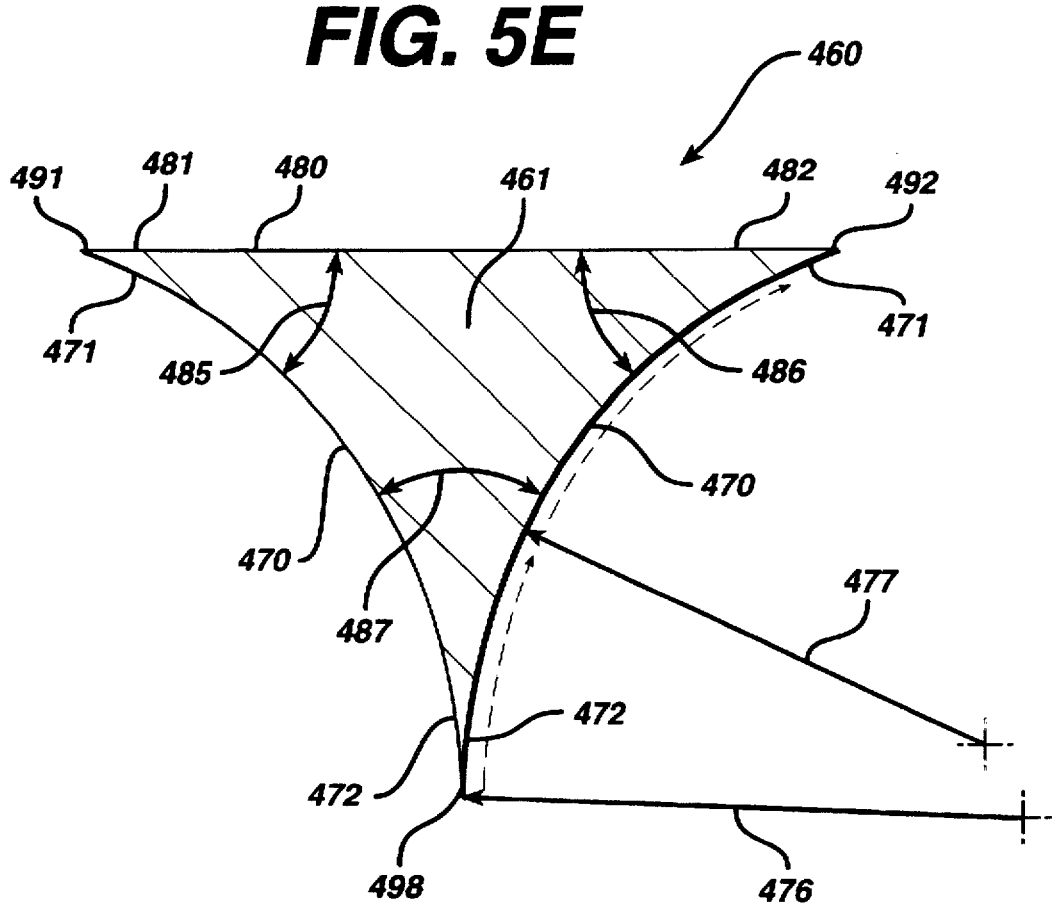

RADIUSED HOLLOW CUTTING EDGE NEEDLE

This is a continuation of application Ser. No. 08/601,899, filed Feb. 15, 1996, now abandoned.

FIELD OF THE INVENTION

The field of art to which this invention relates is surgical needles, in particular, surgical needles having cutting edges.

BACKGROUND OF THE INVENTION

Surgical needles are well known in the medical arts. The needles typically have a curved, elongated body with a distal piercing point and a proximal suture mounting end. Sutures may be mounted either into holes drilled into the proximal ends of the needle or channels stamped into the proximal ends of the needles. Sutures are mounted to the drilled holes or channels through a conventional swaging process wherein the proximal end of a needle is stamped or hit with a die thereby compressing the suture within the hole or channel.

Although there are a variety of surgical needles known in this art, two types of conventional surgical needles are widely and typically used. These needles include taper point needles and cutting edge needles. Taper point needles taper to a distal piercing point and have a smooth outer surface. Cutting edge needles have both a piercing point and one or more cutting edges with an otherwise smooth outer surface. As mentioned previously, cutting edge needles are known in the art and are disclosed for example in U.S. Pat. Nos. 5,002,564; 4,932,961; 5,002,565, and 5,030,228, which are incorporated in their entirety by reference. Cutting edge needles are also disclosed in U.S. Pat. No. 5,476,480.

There is constant need in this art for improved cutting edge needles, having novel geometries which produce improved penetration characteristics. There is also a constant need in this art for cutting edge needles which have configurations that are readily manufactured in an automated manufacturing process.

SUMMARY OF THE INVENTION

Accordingly, it is an object of the present invention to provide cutting edge needles having novel cross-sections which provide for improved penetration into tissue.

It is a further object of the present invention to provide a cutting edge needle having a cross section which is easy to manufacture in automated needle manufacturing processes including, for example, stamping/coining processes.

Therefore, a surgical needle having at least one cutting edge is disclosed. The surgical needle consists of an elongated member, having a proximal end and a distal end. A piercing point extends from the distal end of the member. A suture mounting means extends from the proximal end of the member. The distal end of the member has a cross-section. The cross-section has a top side having first and second opposed edges. The top side defines a substantially straight line. The cross-section also has a first concave side defining a line, said first concave side having a top edge and a bottom edge. The cross-section further has a second concave side defining a line, said second concave side having a top edge and bottom edge. At least a part of each concave side is curved. The top edge of the first concave side and the first opposed edge of the top side are co-extensive forming a first cutting edge. The top edge of the second concave side and the second opposed edge of the top side are co-extensive forming a second cutting edge. In addition, the bottom edges of the first and second concave sides are co-extensive forming a third cutting edge. Preferably, the surgical needle is curved.

Yet another aspect of the present invention is the above described needle wherein the top side is concave and defines a line and wherein at least part of the line defined by the top side is curved.

Still yet another aspect of the present invention is a method of approximating mammalian tissue using the above-described surgical needle and a surgical suture.

Other features and advantages of the cutting edge needles of the present invention will become more apparent from the following description and accompanying drawings.

BRIEF DESCRIPTION OF THE DRAWINGS

FIG. 5E is a cross-sectional view of the distal end of a needle of the present invention having concave sides which define curved lines wherein each curved line has two radii.

DETAILED DESCRIPTION OF THE INVENTION

Figure 1:
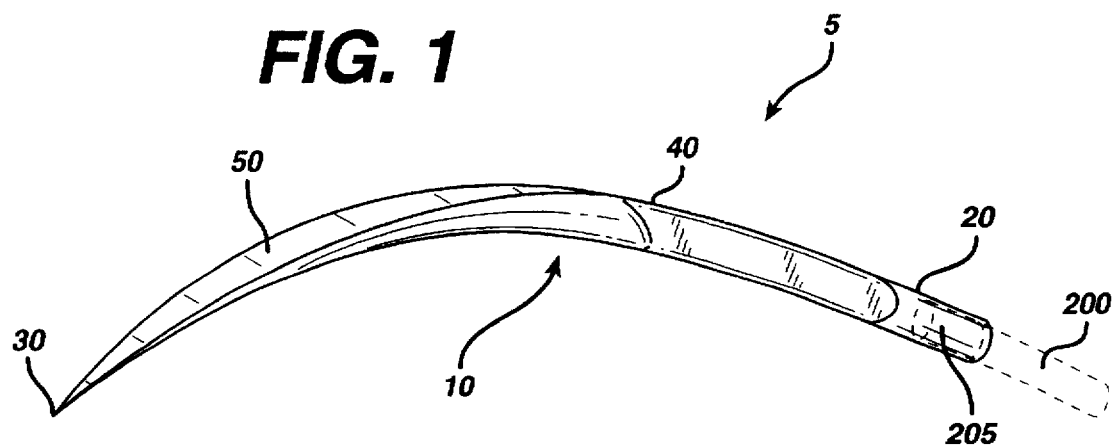
FIG. 1 is a perspective view of a surgical needle of the present invention having a drilled proximal suture mounting cavity.
Figure 5A:
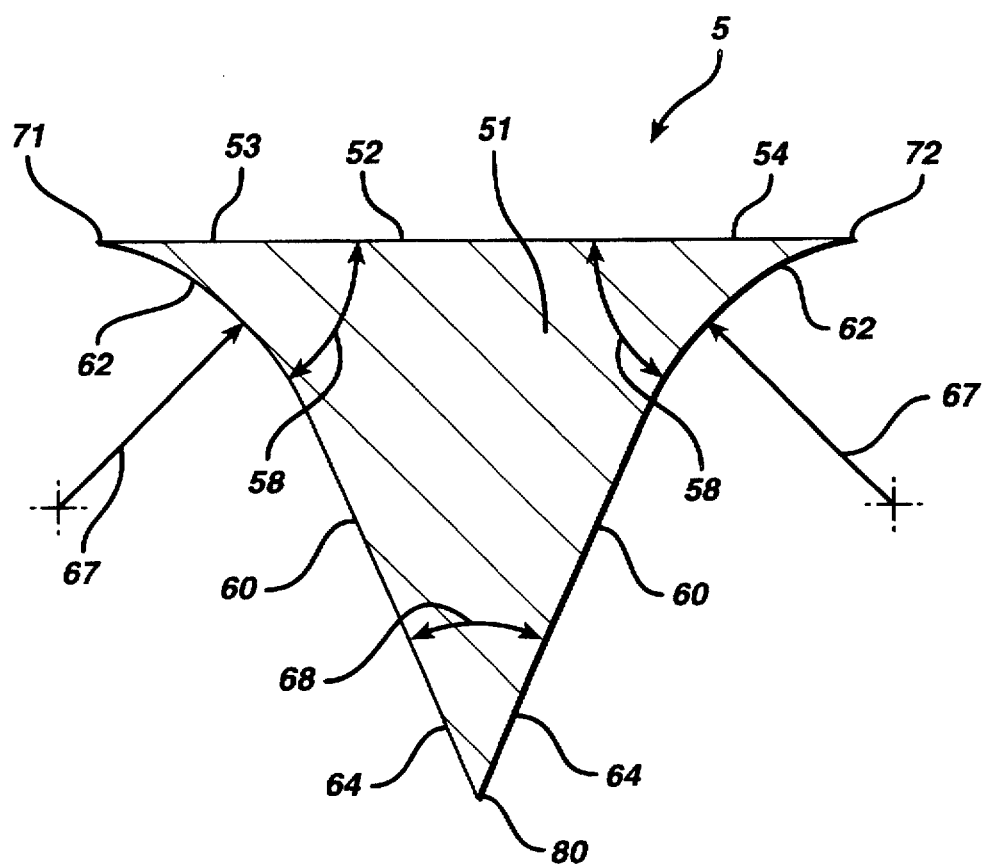
FIG. 5A is a cross-sectional view of the needle of FIG. 2 taken along View Line 5—5.
Figure 5B:
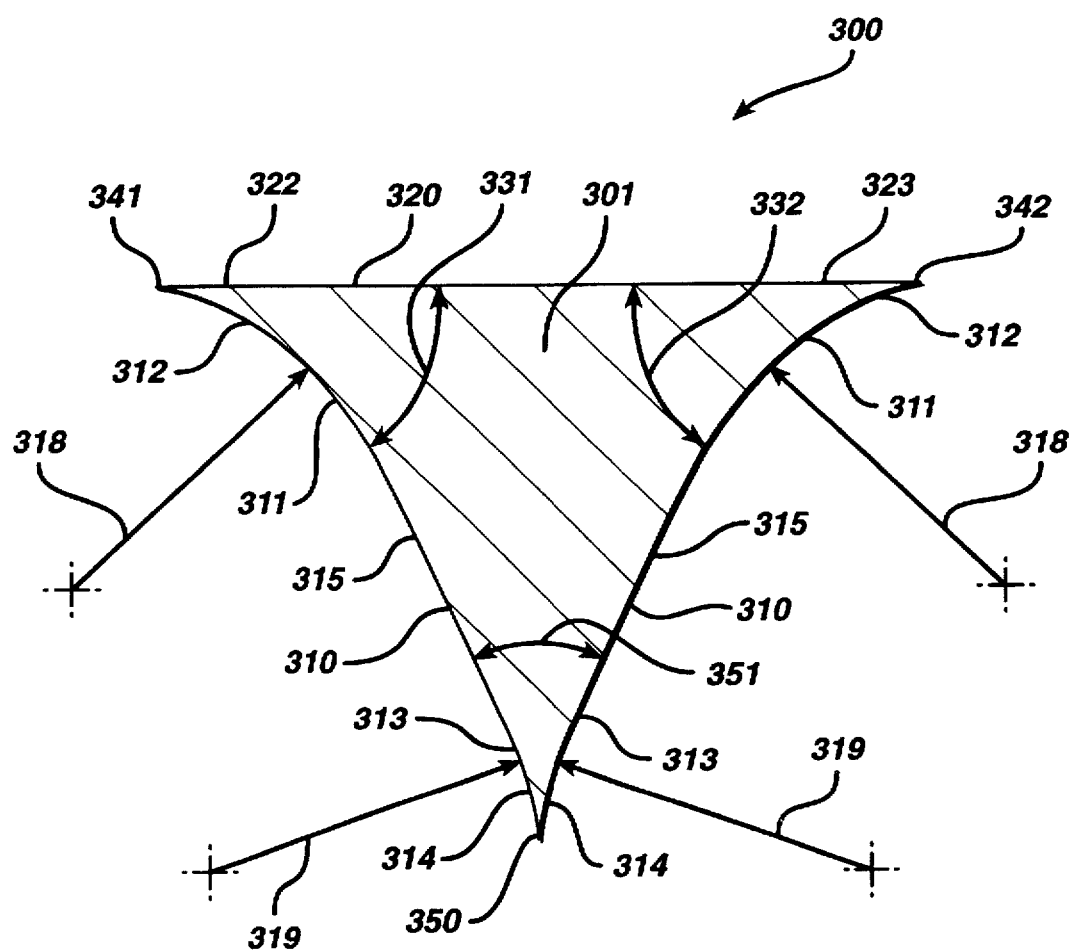
FIG. 5B is a cross-sectional view of the distal end of a needle of the present invention having concave sides which define lines having curved upper sections and lower sections connected by straight intermediate sections.
Figure 5C:
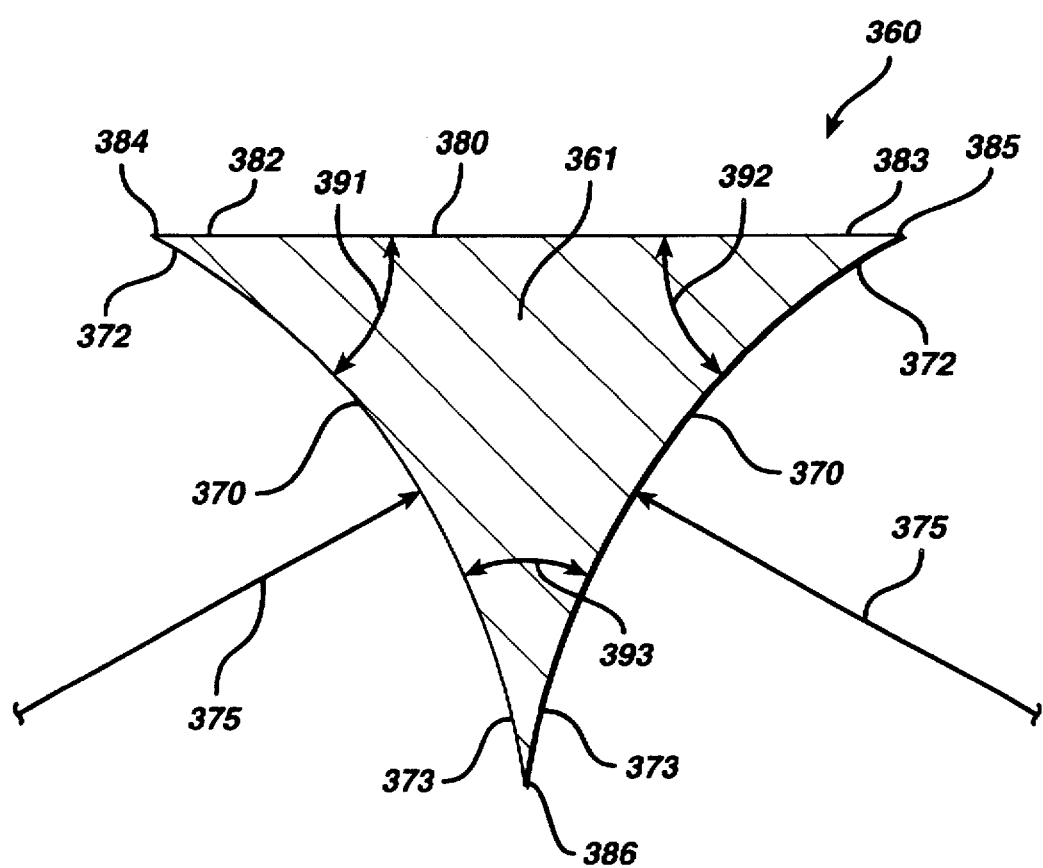
FIG. 5C is a cross-sectional view of the distal end of a surgical needle of the present invention wherein the concave sides define lines which are completely curved.
Figure 5D:
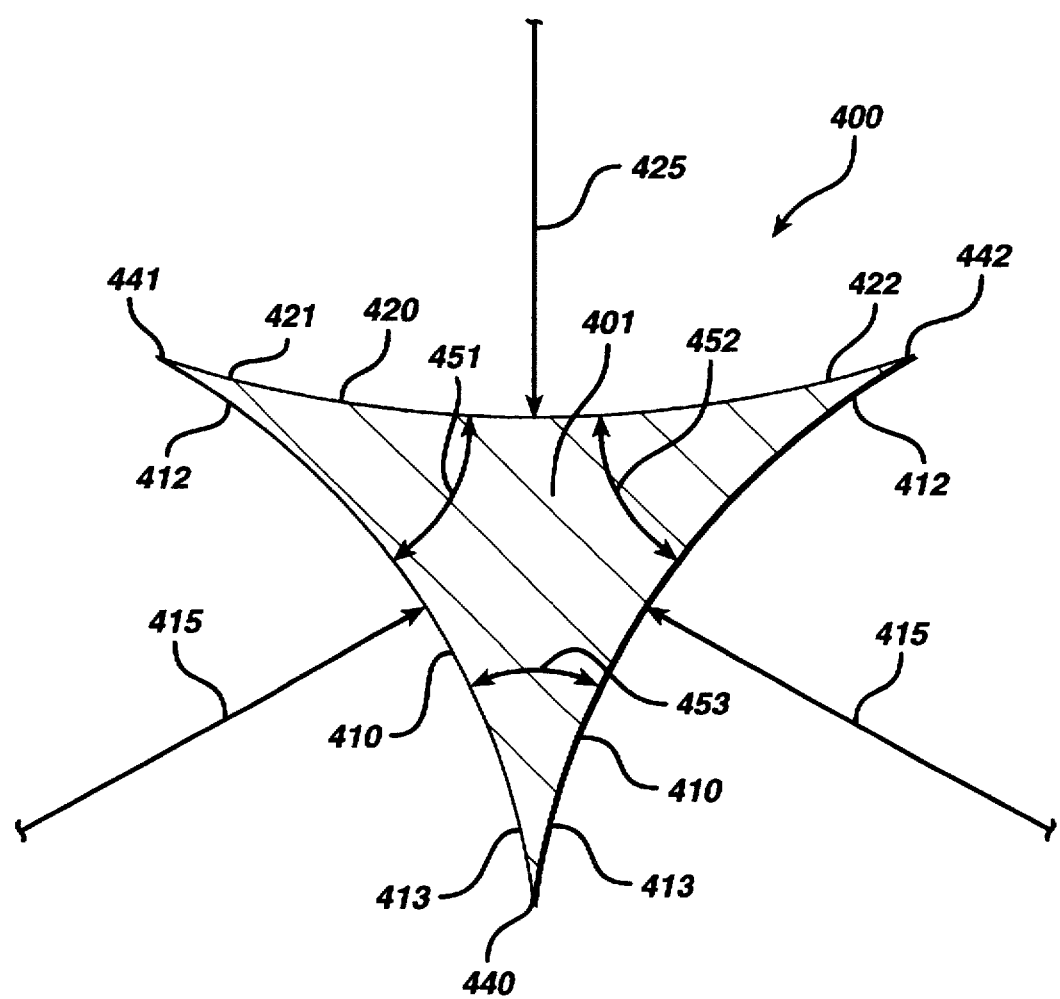
FIG. 5D is a cross-sectional view of the distal end of a needle of the present invention having curved concave sides and a top side defining a curved line.
Figure 6:
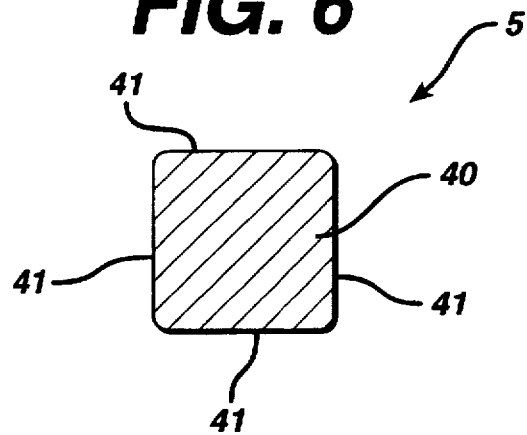
FIG. 6 is a cross-sectional view of the surgical needle of FIG. 1 taken along View Line 6—6.
Figure 7:
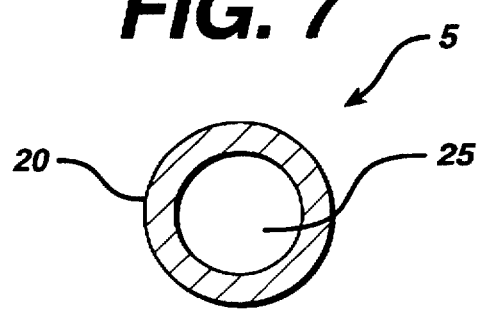
FIG. 7 is a cross-sectional view of the surgical needle of FIG. 1 taken along View Line 7—7.
Figure 12:
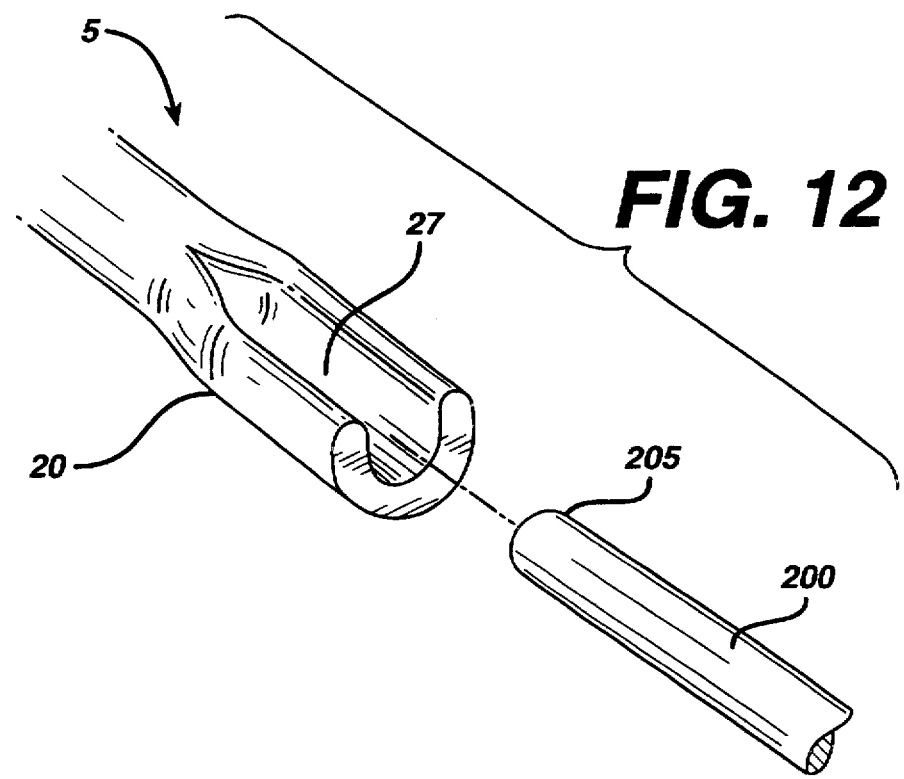
FIG. 12 is a perspective view of a proximal end of a surgical needle of the present invention illustrating a channel suture mounting means.
Figure 13:
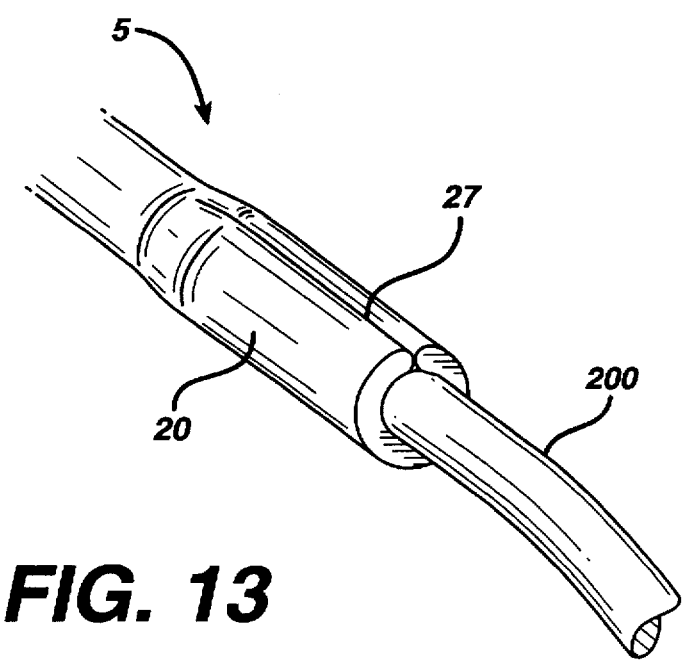
FIG. 13 illustrates the needle of FIG. 12 after a suture has been mounted and swaged into the channel.

As can be seen in FIGS. 1–7, 12, and 13, the cutting edge needle 5 of the present invention is seen to be an elongated member 10, having a proximal end 20, a distal end 50, and a central section 40. The needle 5 is seen to have distal piercing tip 30. Although FIG. 1 shows a conventional curvature of the elongated member 10, it will be appreciated by those skilled in the art that the curvature of elongated member 10 may be reversed such that the orientation is about 180 degrees opposite from that illustrated in FIG. 1. As seen in FIG. 6, central section 40 has a generally square cross-section having opposed surfaces 41. If desired, the cross-section of central section 40 may have other conventional configurations including rectangular, circular, oval, triangular and the like. The cross-section of central section 40 will preferably be such that a conventional needle-grasper can sufficiently grasp and effectively maintain the needle 5 in a fixed position as the needle 5 penetrates body tissue without the needle slipping between the jaws of the needle grasper. Referring to FIG. 7, proximal end section 20 is seen to have a circular configuration, having a central drilled suture mounting hole 25. A conventional surgical suture 200 is illustrated in phantom in FIG. 1 mounted in suture mounting hole 25 of needle 5. A suture 200 is mounted in hole 25 using conventional swaging processes. As seen in FIGS. 12 and 13, the proximal end 20 of the needle 5 may also have a conventional channel section 27 for receiving and mounting a suture 200. The channel 27 is illustrated in FIG. 13 after the distal tip 205 of the suture 200 has been mounted and swaged in a conventional manner therein. The suture mounting hole 25 is drilled in a conventional manner using conventional drilling equipment including mechanical drills, lasers, and the like and combinations thereof. Channel 27 is formed using a conventional forming process wherein the channel is formed using conventional dies and punches. The needles 5 of the present invention may have conventional sharp or blunt distal piercing tips 30.

Figure 2:
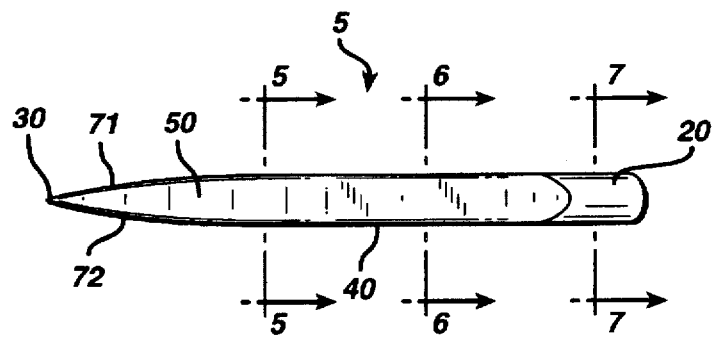
FIG. 2 is a top view of the surgical needle of FIG. 1.
Figure 3:
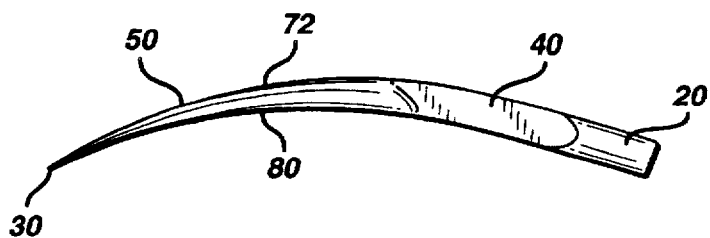
FIG. 3 is a side view of the surgical needle of FIG. 2.
Figure 4:
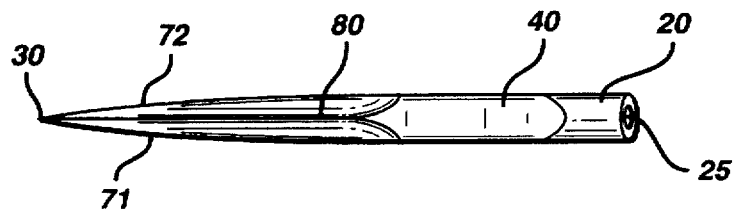
FIG. 4 is a bottom view of the surgical needle of FIG. 1.
Figure 9:
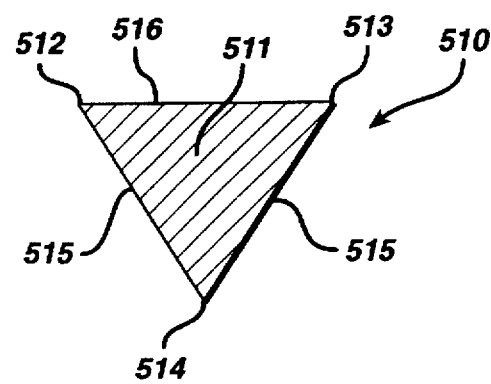
FIG. 9 is a cross-sectional view of the surgical needle of FIG. 8 taken along View Line 9—9.
Figure 10:
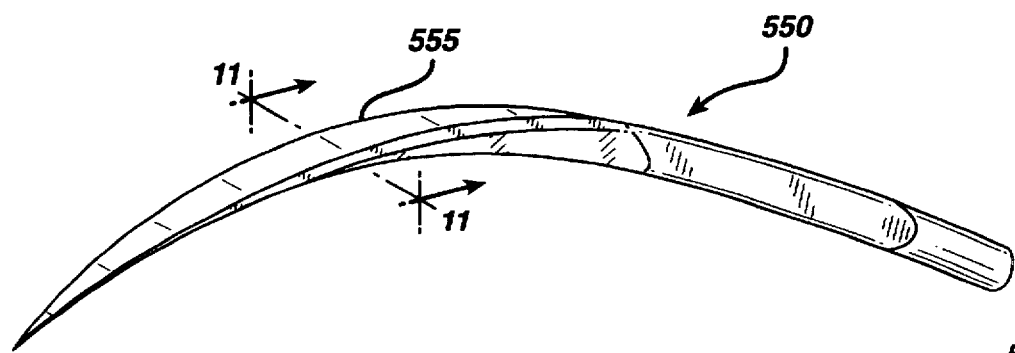
FIG. 10 is a perspective view of another embodiment of a cutting edge surgical needle of the prior art wherein the concave sides consist of multiple straight segments.
Figure 11:
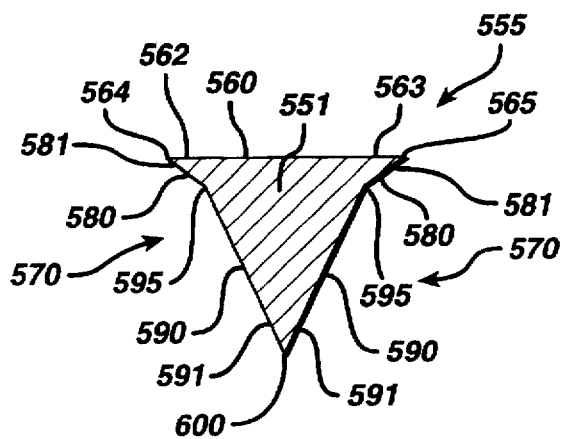
FIG. 11 is a cross-sectional view of the needle of FIG. 10 taken along view line 11—11.

Referring to FIGS. 2 and 5A, a needle 5 of the present invention is illustrated. The needle 5 is seen to have a cross-section 51 at distal end 50. The cross-section 51 is seen to have a top side 52 having first and second opposed edges 53 and 54. The cross-section 51 is also seen to have lateral, opposed, first and second concave sides 60 having top edges 62 and bottom edges 64. The sides 60 are each seen to have a curved section adjacent to top edges 62 having radius 67. The opposed edges 53 and 54 are seen to be co-extensive with the edges 62 to form the cutting edges 71 and 72. It will be appreciated by those skilled in the art that the edges 71 and 72 as seen in FIG. 2 may have various geometric configurations including curved, multiple radiuses, combinations of straight lines and radiuses, equivalents thereof and the like. The bottom edges 64 of the sides 60 are seen to be co-extensive to form the cutting edge 80. It is believed that the cutting edges of the needles 5 of the present invention may be sharper than the cutting edges of conventional cutting edge needles because the included angles 58 and 68 of the cutting edges 71, 72 and 80 may be smaller than the included angles of the cutting edges 510 and 512 on a conventional geometry cutting edge needle 500 as seen in FIG. 9 or the included angles of the cutting edges 564 and 565 of needle 550 as seen in FIGS. 10 and 11. By included angle is meant the angle between coextensive edges, e.g., angle 58 between edges 53 and 62 or edges 54 and 62, and angle 68 between edges 64 of opposed concave sides 60 as seen in FIG. 5A. The included angle 58 of the top cutting edges of the needles of the present invention will be sufficient to provide for effective cutting in tissue. Typically the angles will range from about 10 degrees to about 55 degrees, more typically about 20 degrees to about 45 degrees and preferably about 20 degrees to about 35 degrees. The included angle 68 of the bottom cutting edges of the needles of the present invention will be sufficient to provide for effective cutting through tissue. Typically, the included angle 68 will be about 10 degrees to about 90 degrees, more typically about 20 degrees to about 70 degrees, and preferably about 40 degrees to about 60 degrees. Those skilled in the art will appreciate that radius 67 will be selected to provide for the desired included angle 58 and the desired cross-section and will of course depend upon the wire size of the needle 5. The sum of the included angles for a distal cross-section of the needles of the present invention will be less than 180 degrees.

The sides 60 of the cross-section 51 of section 50 of needle 5 may be configured to have a variety of curved shapes and sections in addition to that illustrated in FIG. 5A including multiple straight sections, circular arc, curvilinear, or combinations of straight and curvilinear or arc sections. For Example, FIG.5B illustrates a cross-section 301 of a needle 300 of the present invention having opposed concave sides 310 defining a line having curved top sections 311 adjacent to top edge 312 having first radius 318, bottom curved sections 313 adjacent to bottom edge 314 having radius 319, and intermediary straight connective sections 315. Cross-section 301 has a flat, straight top side 320 which defines a substantially straight line having first and second oppose edges 322 and 323. Needle 300 is seen to have cutting top cutting edges 341 and 342 and bottom cutting edge 350. Cross-section 301 is seen to have included angle 331 between first opposed edge 322 and top edge 312, included angle 332 between second opposed edge 323 and top edge 312, and angle 351 between bottom edges 314. FIG. 5C illustrates a cross-section 361 of the distal end of a needle 360 of the present invention having opposed concave sides 370 defining a curved line running from top edges 372 to bottom edges 373. Each side 370 is seen to have radius 375. The needle 360 is seen to have a flat, straight top 380 defining a substantially straight line having first and second opposed edges 382 and 383. Needle 360 is seen to have top cutting edges 384 and 385, and bottom edge 386. Cross-section 361 is seen to have included angle 391 between first opposed edge 382 and top edge 372, included angle 392 between second opposed edge 383 and top edge 372, and angle 393 between bottom edges 373. FIG. 5D illustrates a cross-section 401 of the distal end of a needle 400 of the present invention having opposed concave sides 410 defining lines which are curved each having radius 415, top edges 412 to bottom edges 413. The needle 400 is seen to have concave curved top 420 defining a curved line having radius 425, first opposed edge 421 to second opposed edge 422. Needle 400 is seen to have top cutting edges 441 and 442 and bottom cutting edge 440. Cross-section 401 is seen to have included angle 451 between first opposed edge 421 and top edge 412, included angle 452 between second opposed edge 422 and top edge 412, and angle 453 between bottom edges 413. FIG. 5E illustrates a cross-section 461 of a needle 460 of the present invention having curved sides 470 and top edges 471 and bottom edges 472 wherein each side 470 defines a curved line having two curved sections having first and second radii 476 and 477, respectively. Cross-section 461 is seen to have top straight side 480 defining a straight line having first and second opposed edges 481 and 482. Needle 460 is seen to have top cutting edges 491 and 492 and bottom cutting edge 498 and to have included angles 485, 486 and 487. As mentioned previously, those skilled in the art will appreciate that the radiuses of the concave sides of the needles of the present invention will be selected to provide desired included angles, as well as providing desired manufacturablility and penetration resistance.

Figure 8:
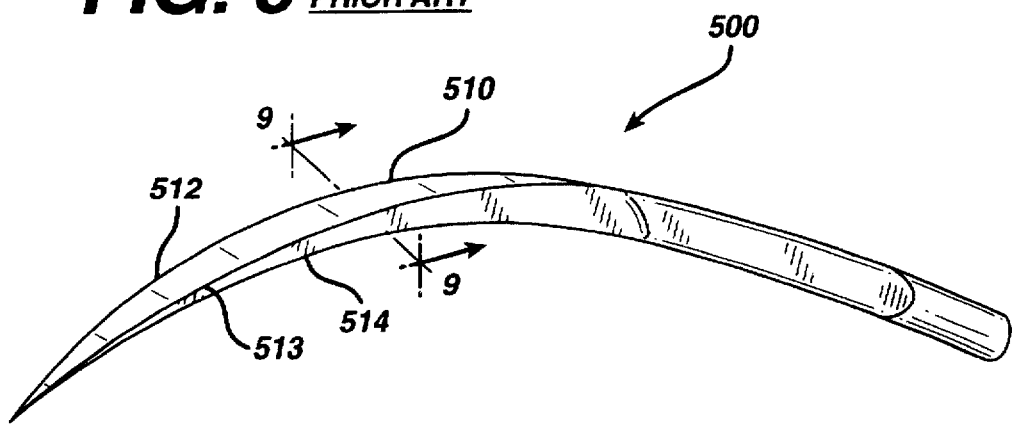
FIG. 8 is a perspective view of a cutting edge needle of the prior art.

Referring to FIG. 8, a needle 500 of the prior art is illustrated. The needle 500 is seen to have a distal end 510 having a triangular cross-section 511 as illustrated in FIG. 9.

The opposed flat lateral sides 515 and top flat side 516 of the cross-section 511 of needle 500 are seen to form a triangular configuration having top cutting edges 512 and 513 and bottom cutting edge 514. Sides 515 and 516 are seen to define substantially straight lines. Although such a configuration provides cutting edges, there are disadvantages associated with this type of configuration. These disadvantages include the fact that improved tissue penetration can only be achieved by lengthening and thereby weakening the cutting edges. In addition, the larger area of this cross-section 511 results in a larger hole and more trauma when passed through tissue.

Another needle 550 of the prior art is illustrated in FIG. 10. FIG. 10 illustrates a cutting edge needle 550 having a cross-section 551 at the distal end 555 as seen in FIG. 11. The cross-section 551 is seen to have a flat top side 560 defining a substantially straight line and having oppose edges 562 and 563, and top cutting edges 564 and 565. The opposed sides 570 of the cross-section 561 are seen to consist of intersecting, straight sides 580 and 590 defining substantially straight lines which are angulated to form an indentation or intersection 595. Intersecting sides 580 and 590 are used to form sides 570 in order to increase the sharpness of the top cutting edges 564 and 565 by decreasing the included angle of these cutting edges, i.e., the angle between edges 562 and 563 and edges 581. Side 580 is seen to have upper edge 581. Side 590 is seen to have lower edge 591. The needle 550 has top cutting edges 564 and 565 and bottom cutting edge 600. Although the needle 550 is believed to have adequate performance characteristics, this geometry or configuration is believed to be difficult to manufacture due to the resistance to metal flow during die forming around the intersection 595 of surfaces 580 and 590.

The needles of the present invention will be manufactured in a variety of sizes, curved configurations and wire diameters. The exact size and curvature of the needles of the present invention is, of course, a matter of choice. The diameter of the needle wire used to manufacture the needles of the present invention will depend upon the particular needle size and intended use. For example, the needle wire may have a diameter ranging from 0.001 inches to about 0.100 inches, more typically about 0.010 inches to about 0.080 inches, preferably about 0.015 inches too about 0.080 inches. However, other wire diameters may be used. The length of the needles of the present invention will vary in accordance with several parameters including the wire alloy, the wire diameter the desired finished length and the type of needle. The radius of curvature will generally be anywhere from 0.050 inches to about 6 inches. The length of the arc will be anywhere, depending on choice, from about ¼ to about ⅝ of a circle. By choice, naturally, some needles will remain straight. Optionally the needles 5 can have curved and straight sections. The needles of the present invention may be made from conventional alloys including 300 series stainless steel, 400 series stainless steel or any other alloys or materials( e.g., polymers, ceramics, etc.) which can be formed into a needle or equivalents thereof having sufficient mechanical characteristics to produce a needle which effectively functions.

The needles of the present invention may be made using conventional cutting edge surgical needle apparatuses and manufacturing methods including die forming, die casting, powdered metal molding, and machining. It is preferred to manufacture the needles of the present invention using equipment and processes as disclosed in commonly-owned U.S. patent application Ser. No. 08/405,554 which is incorporated herein by reference.

The surgical needles of the present invention are believed to have the several surprising and unexpected advantages including ease of tissue penetration, improved tip strength reduced tissue trauma, and better cosmetic results. In addition, manufacturing may be facilitated, especially when using automated manufacturing equipment, including but not limited to stamping/coining.

The needles of the present invention when mounted to conventional surgical sutures are used in a conventional manner in conventional surgical procedures to pass through and approximate mammalian tissue. In such procedures, the needle is typically held in a conventional needle grasper.

Although this invention has been shown and described with respect to detailed embodiments thereof, it will be understood by those skilled in the art that various changes in form and detail thereof may be made without departing from the spirit and scope of the claimed invention.

We claim:

1. A surgical needle having a cutting edge, comprising:

an elongated member having a proximal end and a distal end wherein the elongated member is curved;

a piercing point extending from the distal end of said member;

a suture-mounting means in the proximal end of the member;

wherein the distal end of the member has a cross-section, said cross-section comprising:

a top side having first and second opposed edges, the top side defining a line;

a first opposed lateral concave side having a top edge and a bottom edge, the first concave side defining a line at least part of which is curved such that the concave side comprises at least one curved section and at least one straight section;

a second, opposed lateral concave side having a top edge and a bottom edge, the second concave side defining a line at least part of which is curved such that the concave side comprises at least one curved section and at least one straight section, wherein the top edge of the first opposed side and the first opposed edge of the top surface are co-extensive to form a first cutting edge, and wherein the top edge of the second opposed side and the second opposed edge of the top are co-extensive to form a second cutting edge, and wherein the bottom edges of the first and second side surfaces are co-extensive to form a third cutting edge.

2. The needle of claim 1 wherein the suture-mounting means comprises a drilled cavity.

3. The needle of claim 1 wherein the suture-mounting means comprises a channel.

4. The needle of claim 1 wherein the piercing point comprises a blunt tip.

5. The needle of claim 1 wherein the piercing point comprises as sharp piercing point.

6. The needle of claim 1 wherein each concave side defines a line comprising a first curved section adjacent to the top edge, a second curved section adjacent to the bottom edge and a straight section connecting the two curved sections.

7. The needle of claim 1 wherein the first concave side comprises a line having a curved section adjacent to the top edge.

8. The needle of claim 1 wherein the second concave side comprises a line having a curved section adjacent to the top edge.

9. The needle of claim 1 wherein the first concave side comprises a line having a curved section adjacent to the bottom edge.

10. The needle of claim 1 wherein the second concave side comprises a line having a curved section adjacent to the bottom edge.

11. The needle of claim 1 comprising an included angle between the intersection of the top edge of the first concave side and the first opposed edge of the top side of about 10 degrees to about 55 degrees.

12. The needle of claim 1 comprising an included angle between the intersection of the top edge of the second concave side and the second opposed edge of the top side of about 10 degrees to about 55 degrees.

13. The needle of claim 1 comprising an included angle between the intersection of the bottom edges of the first and second concave sides of about 10 degrees to about 90 degrees.

14. The needle of claim 1 wherein the elongated member is straight.

15. A method of approximating mammalian tissue, said method comprising:

inserting a surgical needle having an attached surgical suture through mammalian tissue thereby approximating the tissue, wherein the surgical needle comprises:
an elongated member having a proximal end and a distal end wherein the elongated member is curved;
a piercing point extending from the distal end of said member;
a suture-mounting means in the proximal end of the member;

wherein the distal end of the member has a cross-section, said cross-section comprising:

a top side having first and second opposed edges, the top side defining a line;
a first opposed lateral concave side having a top edge and a bottom edge, the first concave side defining a line at least part of which is curved such that the concave side comprises at least one curved section and at least one straight section;

a second, opposed lateral concave side having a top edge and a bottom edge, the second concave side defining a line at least part of which is curved such that the concave side comprises at least one curved section and at least one straight section, wherein the top edge of the first opposed side and the first opposed edge of the top surface are co-extensive to form a first cutting edge, and wherein the top edge of the second opposed side and the second opposed edge of the top are co-extensive to form a second cutting edge, and wherein the bottom edges of the first and second side surfaces are co-extensive to form a third cutting edge.

* * * * *